(12) United States Patent
Fleischer et al.

(10) Patent No.: US 8,360,118 B2
(45) Date of Patent: Jan. 29, 2013

(54) FUEL SYSTEM FOR A FLOATING UNIT, AND METHOD FOR THE OPERATION THEREOF

(75) Inventors: Maximilian Fleischer, Höhenkirchen (DE); Uwe Lampe, Buxtehude (DE); Hans Bernhard Müller-Schwenn, Hamburg (DE); Kerstin Wiesner, Putzbrunn (DE)

(73) Assignee: Siemens Aktiengesellschaft, Munich (DE)

( * ) Notice: Subject to any disclaimer, the term of this patent is extended or adjusted under 35 U.S.C. 154(b) by 400 days.

(21) Appl. No.: 12/678,568

(22) PCT Filed: Aug. 29, 2008

(86) PCT No.: PCT/EP2008/061367
§ 371 (c)(1),
(2), (4) Date: Mar. 17, 2010

(87) PCT Pub. No.: WO2009/037089
PCT Pub. Date: Mar. 26, 2009

(65) Prior Publication Data
US 2010/0200104 A1    Aug. 12, 2010

(30) Foreign Application Priority Data

Sep. 19, 2007  (DE) .................. 10 2007 044 970
May 2, 2008    (DE) .................. 10 2008 021 899

(51) Int. Cl.
*B65B 1/30*  (2006.01)
*G05D 11/02* (2006.01)

(52) U.S. Cl. ............ 141/94; 366/152.1; 366/152.2
(58) Field of Classification Search .......... 141/83, 141/94; 366/151.1, 152.1, 152.2
See application file for complete search history.

(56) References Cited

U.S. PATENT DOCUMENTS

| 4,541,272 A | * | 9/1985 | Bause ................ 73/114.72 |
| 4,553,032 A |   | 11/1985 | Borken |
| 5,343,906 A | * | 9/1994 | Tibbals, III ............ 141/83 |
| 5,348,645 A |   | 9/1994 | Maggard |
| 5,722,469 A | * | 3/1998 | Tuminaro ............ 141/94 |

(Continued)

FOREIGN PATENT DOCUMENTS

| CH | 633612 A5 * 12/1982 |
| WO | 96/00380    1/1996 |

(Continued)

OTHER PUBLICATIONS

On-Board Elemental XRF Analysis of Oils & Additives; SEA-Mate TM, A Joint Venture of Maersk Fluid Technology and Innov-X Systems; Maersk Fluid Technology.
Information Search Report, Feb. 2, 2009.

*Primary Examiner* — Lisa Caputo
*Assistant Examiner* — Punam Roy
(74) *Attorney, Agent, or Firm* — Harness, Dickey & Pierce, P.L.C.

(57) ABSTRACT

A fuel system is disclosed for a floating unit, including a fuel passage extending from a filler neck to a motor, a measuring unit disposed in the fuel passage through which at least part of the fuel flowing along the fuel passage flows, for measuring a sulfur content of the fuel through the measuring unit.

16 Claims, 6 Drawing Sheets

U.S. PATENT DOCUMENTS

| | | | |
|---|---|---|---|
| 6,341,629 B1 * | 1/2002 | Clark et al. | 141/83 |
| 6,712,102 B2 * | 3/2004 | Zerangue, Sr. | 141/83 |
| 6,859,517 B2 * | 2/2005 | Wilson et al. | 378/47 |
| 7,983,851 B2 * | 7/2011 | Jensen | 702/25 |
| 2009/0317299 A1 * | 12/2009 | Rebinsky et al. | 422/82.08 |
| 2010/0039884 A1 * | 2/2010 | Weathers et al. | 366/152.2 |
| 2012/0096923 A1 * | 4/2012 | Weinstein et al. | 73/19.03 |

FOREIGN PATENT DOCUMENTS

| | | |
|---|---|---|
| WO | WO 9600380 A1 | 1/1996 |
| WO | 2007/042051 | 4/2007 |
| WO | WO 2007042051 A1 | 4/2007 |
| WO | 2007/093500 | 8/2007 |
| WO | WO 2007093500 A1 | 8/2007 |

* cited by examiner

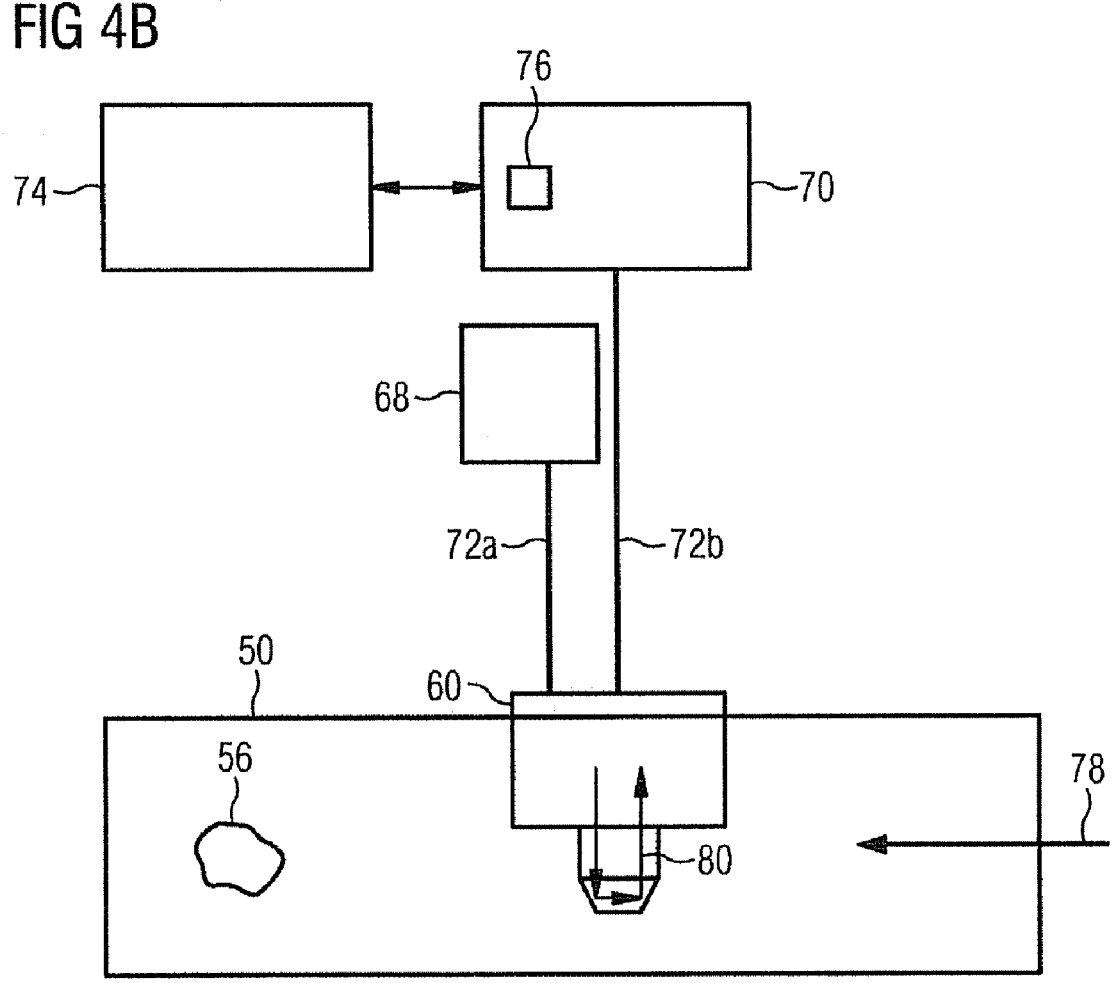

FUEL SYSTEM FOR A FLOATING UNIT, AND METHOD FOR THE OPERATION THEREOF

PRIORITY STATEMENT

This application is the national phase under 35 U.S.C. §371 of PCT International Application No. PCT/EP2008/061367 which has an International filing date of Aug. 29, 2008, which designates the United States of America, and which claims priority on German patent application numbers DE 10 2007 044 970.6 filed Sep. 19, 2007, and DE 10 2008 021 899.5 filed May 2, 2008, the entire contents of each of which are hereby incorporated herein by reference.

FIELD

At least one embodiment of the invention generally relates to a fuel system for a floating unit and/or to a method for the operation thereof.

BACKGROUND

Floating units in the context of the present document are, for example, ocean-going craft, such as ships or submarines, or else fuel-consuming offshore installations, such as drilling rigs or wind power plants. For the sake of simplicity, to represent these, ships are referred to hereafter.

Fuels for ships (often also designated, in this context, as "propellants" or "combustibles") are distinguished by a high sulfur content of up to 5% by weight. Since shipping has increased greatly in recent years due to increasing international trade, its share of environmental pollution in harbors and inshore waters has risen markedly. Thus, in particular, the sulfur-containing exhaust gas constituents, such as $SO_2$, are especially harmful. There has therefore, for some time, been efforts to limit the sulfur emissions by ships by limiting the sulfur content of the fuels. For the SECAS ($SO_x$ EMISSIONS CONTROLLED AREAS) of the North Sea and Baltic Sea, it is prescribed, for example, that only fuels with a maximum sulfur content of 1.5% by weight, and in harbors even only sulfur-free fuels (content <0.1% by weight), should be used. Similar regulations apply on the West coast of the USA. When traveling in these waters, ships are monitored as to whether only fuels with a content below the prescribed limit are currently being employed. There is a threat of severe penalties in the event of violations.

Furthermore, outside the statutory sea areas, fuel with any sulfur content is allowed to be burnt on the world's oceans. Since low-sulfur fuel is more costly than fuel with a high sulfur content, ships are operated with cheap sulfur-containing fuel over most of their trip and low-sulfur fuels are used only in specific areas. This means that, in future, ships will bunker fuels having different qualities.

EU Directive 2005/33/EC provides,
  from 11 Aug. 2006, for the introduction of a sulfur limit value of 1.5% for ship's fuels which are used by ships in the Baltic Sea and, from 11 Aug. 2007, in the North Sea and in the English Channel, in order to reduce acidification and improve the air quality,
  from 11 Aug. 2006, for the introduction of a sulfur limit value of 1.5% for ship's fuels which are used by passenger ships in a scheduled service from or to a Community harbor, so that the air quality is improved and, in order to ensure an EU-wide supply of low-sulfur ship's fuels, a sufficient demand is afforded,
  for the introduction of a sulfur limit value of 0.1% from 1 Jan. 2010 for ship's fuels which are used by ships on the inland waterways and at berths for diesel engines, so that the air quality in harbors and on inland waterways is improved,
  contrary to the above-described limit values for heavy oils, for issuing a permit to ships for the use of an approved emission-reducing technology, insofar as these ships constantly achieve at least equivalent emission reductions and it is documented in detail that all waste flows discharged to closed harbors and river mouths have no effect on the ecosystems,
  for the proper management of logbooks with indications of the fuel changeover to become a condition for ships to be able to enter harbors of the EU Community,
  for the sulfur content of all fuels sold in the sovereign area of the member states of the EU to have to be noted by the supplier on a delivery note accompanied by a sample,
  for samples of ship's fuels to be taken and checked for their sulfur content.

A serious problem is that the fuel quality is stipulated internationally in very different ways and not by generally valid laws or standards. In particular, it is to be expected, for example in harbors in Asia, South America or Africa, that the fuel is sold with false certificates, that is to say the sulfur content is usually higher than acknowledged in the certificate. Since, during controls in the areas of limited emissions, not only are the certificates inspected, but direct samples of the fuel are also taken and investigated, the ship's captain may be presented with considerable problems when too high a sulfur content is found (financial penalties, disposal of the false fuel, etc.).

The knowledge of the sulfur content of the fuel has not hitherto been necessary in order to operate a ship, since a limitation of the sulfur emissions for ships in specific sea areas has been implemented for only a very short time. The EU first decided in 2003 upon measures for limiting the sulfur content, the implementation of which is provided for in stages up to 2010. A lowering of the sulfur content to 1.5% by weight for the fuel of ocean-going ships (this applies to SECAS North Sea and Baltic Sea) is provided for 2007.

The sulfur content is at the present time usually measured only when the fuel is produced at the refinery. The ship's captain then has to trust in the correctness of the certificate, but without being able to check it himself.

From [Innov-X-Systems/Maersk Fluid Technology, "On-Board Elemental XRF Analysis of Oils & Additives", 2006], an appliance, referred to as a "Sea-Mate™", is known, which, for example, can be operated on a ship and can investigate samples of fuels with regard to their sulfur content. However, the sampling and subsequent analysis are complicated and time-consuming.

SUMMARY

At least one embodiment of the present invention, therefore, specifies an improved fuel system for a floating unit and an improved method for the operation thereof.

With regard to the fuel system of at least one embodiment, a fuel system is specified for a floating unit, say a ship, with the following features: the fuel system comprises a fuel path which extends from a filler neck for fueling the ship as far as an engine located on the ship. According to at least one embodiment of the invention, a measuring device is arranged in the fuel path. At least part of the fuel which moves along the fuel path flows through this measuring device. In other words, the measuring device is, for example, connected in series into the fuel path or is connected in parallel to the latter in the manner of a bypass. Consequently, the fuel flowing along the fuel path can flow or flows through the measuring device. The measuring device is one which measures a sulfur content of the fuel flowing through the measuring device.

By virtue of at least one embodiment of the invention, therefore, a constant measurement, in other words an online measurement, of the fuel quality with regard to sulfur content in the fuel path of the ship can be implemented. The ship's captain is consequently informed of the fuel quality in that section of the fuel path where measurement takes place. For the location of measurement, there are many possibilities which are explained further below and can also be combined with one another. There does not need to be any complicated sampling at a specific point along the fuel path and analysis elsewhere, for example in a laboratory. The sulfur content can be determined directly on the spot and constantly.

Since the sulfur content of the fuel can be determined in a simple way at any time by way of an online measuring system, the quality and quality control requirements of the ship's fuel according to EU Directive 2005/33/EC can be fulfilled in an uncomplicated way.

In an advantageous embodiment of the invention, the measuring device comprises a light source for irradiating the fuel with light. Moreover, it comprises a detector for light which, emanating from the light source, has irradiated the fuel or been reflected by the fuel. In other words, the sulfur content is determined by means of a transmission or reflection measurement on the fuel. Such a measuring arrangement can easily be installed in the flow path, for example in a fuel line.

For the measurement, for example, IR spectroscopy is suitable. In an advantageous refinement of the invention, therefore, the light source may be an IR light source. In particular, the light source can then radiate in the NIR or MIR range.

In a further example embodiment, the detector is then an IR spectrometer. This is suitable especially in cooperation with the abovementioned light source.

IR spectroscopy is based on the absorption of IR light, with the result that molecular oscillations and/or rotations are excited. A distinction is made between the far infrared range (FIR, wavelength: 30-3000 µm), the medium infrared range (MIR, wavelength: 2.5-30 µm) and the near infrared range (NIR, wavelength: 0.8-2.5 µm).

In the FIR range, the molecular rotations are excited, in the MIR range the molecular fundamental oscillations are excited, and in the NIR range the harmonic and combination oscillations are excited. For analytical purposes, MIR and NIR spectroscopy are preferably employed. The basis for this is that, fundamentally, the oscillation frequency and therefore the wavelength of the absorbed IR light are dependent on the specific strength of the chemical bond and on the mass of the oscillating atoms or atom groups.

The intensity depends on the strength of the dipole moment of the atom group to be excited and on the concentration. IR spectroscopy therefore gives information on the qualitative nature of the absorbing species and its quantitative fraction in a mixture.

The advantage of MIR spectroscopy is that it gives information on individual localized atom groups, which information can be assigned to a specific chemical species. This makes it easier to identify them. In particular, organic sulfur compounds can easily be identified, above all since the mass of the sulfur atom is high in comparison with other atoms of an organic compound (shift of absorption toward higher wavelengths). The disadvantage of MIR spectroscopy is that this method can be implemented as an online measuring method only at a high outlay. This refers particularly to the required measuring cells and optical fibers.

NIR spectroscopy makes it possible only exceptionally to assign the measured absorptions to specific molecules or molecule groups, and, furthermore, the absorption of NIR radiation is markedly lower than that of MIR radiation. This is advantageous, however, since the lower absorption can be compensated by way of a longer optical path length. It is advantageous that NIR spectroscopy can be implemented as an online method at an outlay which is markedly reduced, as compared with the MIR method. This refers, above all, to the measuring cells and optical fibers.

The longer optical path lengths required are also advantageous, since they allow a set-up which is less sensitive to contamination and which is easier to clean.

Since the sulfur content in ship's fuels is caused by a series of organic sulfur compounds, mostly thiols ($C_xH_y$—SH), thioethers ($C_{x1}H_{y1}$—S—$C_{x2}H_{y2}$), heteroaromatics (for example, $C_4H_4S$ thiophene) or disulfides ($C_{x1}H_{y1}$—S—S—$C_{x2}H_{y2}$), the position and intensities of a plurality of absorption bands are preferably incorporated into a quantitative determination of the overall sulfur content. This is possible, using multivariate evaluation methods or a combination of multivariate methods with neural networks. A calibration of the IR spectra can take place with the aid of sulfur concentrations in the ship's fuel which are determined in the laboratory by means of standard methods.

In a further advantageous embodiment, the measuring device may comprise an evaluation unit for the multivariate evaluation of the light irradiating the fuel or reflected by the fuel.

IR spectroscopy, particularly in conjunction with multivariate evaluation (chemometry, ANN) of the spectra, allows an online measurement of the sulfur content of ship's fuel during the bunkering of the fuel and also during the operation of the ship.

In a further advantageous embodiment of the invention, the measuring device may be arranged in an inlet portion of the fuel path, through which inlet portion fuel flows at least during the bunkering operation. Thus, the fuel flowing from the filler neck to the fuel tank during the bunkering operation is monitored online with regard to its sulfur content.

If the correct sulfur content is determined by online measurement as early as during the bunkering of the fuel, the ship's captain can, for example, monitor whether he is receiving fuel of the desired quality and is therefore adhering to the abovementioned provisions. The result measurement could then be used as evidence before authorities.

In a further advantageous embodiment, the measuring device may be arranged in a section of the fuel path through which fuel flows at least during the operation of an engine of the floating unit. By way of online measurement during operation, the ship's captain can at the same time be advised that the supply of the engine has been changed over in due time to the low-sulfur fuel before entry to the area of limited emission.

In a further advantageous embodiment of the invention, a logging device for logging the sulfur content determined by the measuring device may be present in the fuel system. Such a log can be used by the ship's captain as proof, for example, before authorities, in order to demonstrate the correct fuel quality.

A further advantageous embodiment of the fuel system is equipped with at least two fuel tanks for fuels of different sulfur content. Thus, a changeover between the two fuels, for example between the open ocean and inshore waters, is possible.

A mixing device for the mixing of fuels of the fuel tanks and a regulating device, cooperating with the measuring device, for regulating the mixture ratio of the fuels are then additionally provided in an especially advantageous way. Thus, for example, fuel blending can be achieved, so that the sulfur content in the fuel to be burnt always lies just below the permitted limit values.

The mixer may in this case also be a simple changeover device for the two different fuels, if variable blending is not desired.

The online measurement of the fuel quality thus makes it possible to have a type of operation in which low-sulfur and sulfur-containing fuel are mixed cost-effectively, so that, ultimately, a fuel having the maximum permitted sulfur concentration is burnt. The data measured online can therefore be used directly for process control and be logged for the required, for example official evidence.

According to at least one embodiment of the invention, a measuring probe for determining the sulfur content may therefore be installed, for example, in the bunker lines of heavy and diesel oil, approximately 1 m downstream of the bunker flange, in the fuel line upstream of the main engine, in the fuel lines upstream of diesel generator sets and, if appropriate, upstream and downstream of mixing and blending devices or assemblies in fuel systems for heavy oil.

At least one embodiment of the invention therefore allows a direct control of the sulfur content of the fuel during bunkering. This is important particularly in harbors outside the EU and the USA. The ship's captain can immediately discontinue the supply of fuel having too high a sulfur content. The ship's captain can demonstrate before the authorities, on the basis of the automatically set-up bunker log, that fuel with a sulfur content below the statutory limit is on board. In the case of mixed operation (sulfur-containing fuel at sea and low-sulfur fuel in coastal waters), the changeover of fuel types which has taken place can be checked upon entry into the areas with emission limitation and be demonstrated by the log.

It is consequently possible to travel long distances with cost-effective sulfur-containing fuels, and at the same time the use of the prescribed fuel for coastal waters with the emission limitation can be proved. On the basis of online measurement, fuel blending (mixing of sulfur-containing and low-sulfur fuel) can be carried out in order to operate the ship. This makes it possible that essentially only two types of fuel are required (sulfur-containing and sulfur-free).

All the permitted intermediate stages of sulfur concentrations can then be set cost-effectively by means of a corresponding mixing of the fuels.

The use of IR spectroscopy, when employed as an online method for determining the sulfur concentration in the fuel, affords the advantage that the use of the correct fuel can be proved. Costly check analyses in a laboratory are consequently unnecessary. The shipowner can protect himself against the adverse consequences of bunkering with false fuel (inter alia, penalty payments, disposal of the false fuel). The ship can always use the most cost-effective fuels. The environmental pollution caused by sulfur emissions in inshore waters and harbors can be lowered.

With regard to the method of at least one embodiment, a method is disclosed for operating a floating unit, the latter having a fuel system with a fuel path extending from a filler neck as far as an engine. In the method, by means of a measuring device arranged in the fuel path, the sulfur content in that part of the fuel which flows through the measuring device is measured. In this case, at least a part of the fuel which flows along the fuel path flows through the measuring device.

The method of at least one embodiment, together with its advantages, has already been explained in connection with the fuel system.

Preferred uses of the method according to at least one embodiment of the invention and of the device according to at least one embodiment of the invention are therefore in the measurement, in particular online measurement, of the sulfur content of a fuel during the bunkering of the fuel in a ship, of fuels when a ship is operated with different fuels and in fuel blending during the operation of a ship.

BRIEF DESCRIPTION OF THE DRAWINGS

For a further description of the invention, reference is made to the example embodiments of the drawings. In these, in each case in a basic diagrammatic sketch.

DETAILED DESCRIPTION OF THE EXAMPLE EMBODIMENTS

Figure 1:
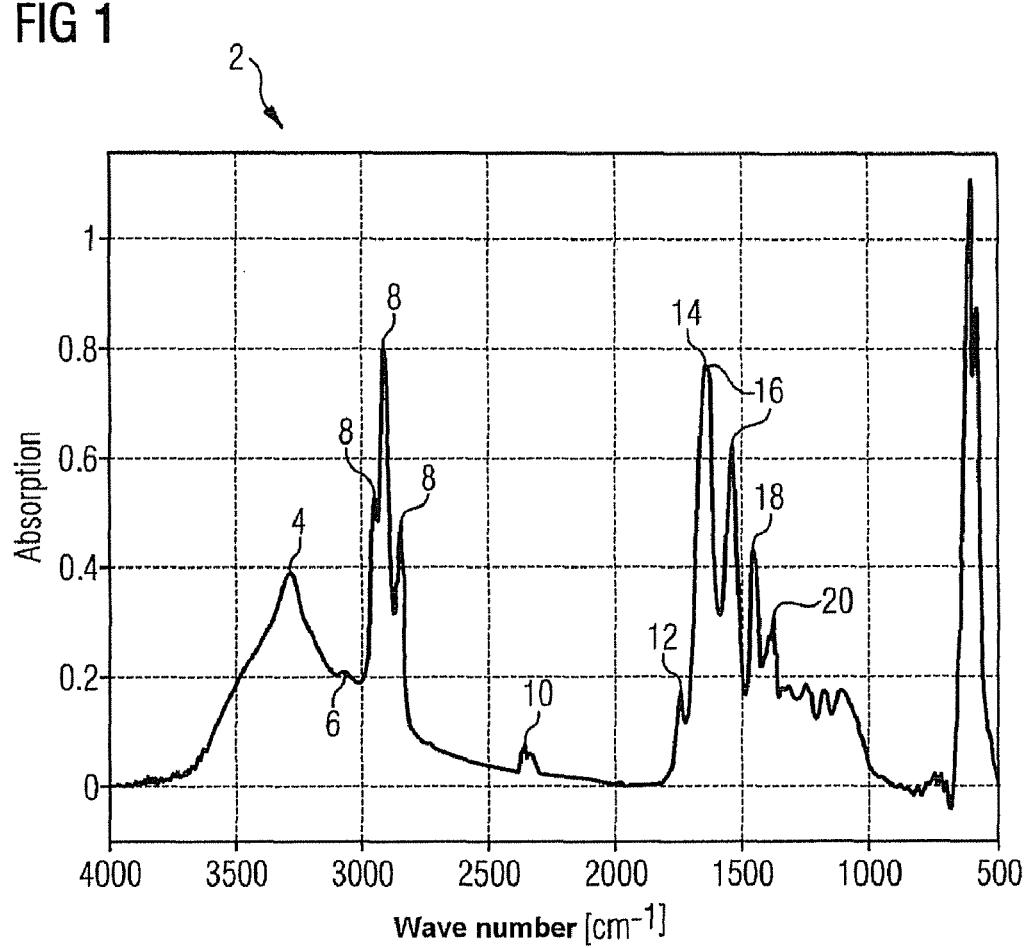
FIG. 1 shows the MIR spectrum of ship's diesel with a 0.16% sulfur content.

FIG. 1 shows a graph 2 which reproduces the MIR spectrum of ship's diesel with 0.16% sulfur. The spectrum was recorded by way of an FTIR appliance (Bruker ifs 66v) in the region of a wave number of between 4000-500 $cm^{-1}$ with a resolution of 4 $cm^{-1}$, using the ATR technique, and was plotted on the abscissa of the graph 2. The ordinate shows the absorption in arbitrary units. What can be seen in particular are the OH and NH valency 4, the C=C—$H_2$ valency 6, the CH valency 8, the location of $CO_2$ 10, that is to say air, the C=O valency 12 or ketone aldehyde, the C=C location 14, aromatic 16, the CH deformation 18 and the —$CH_3$-symmetrical deformation 20.

Figure 2:
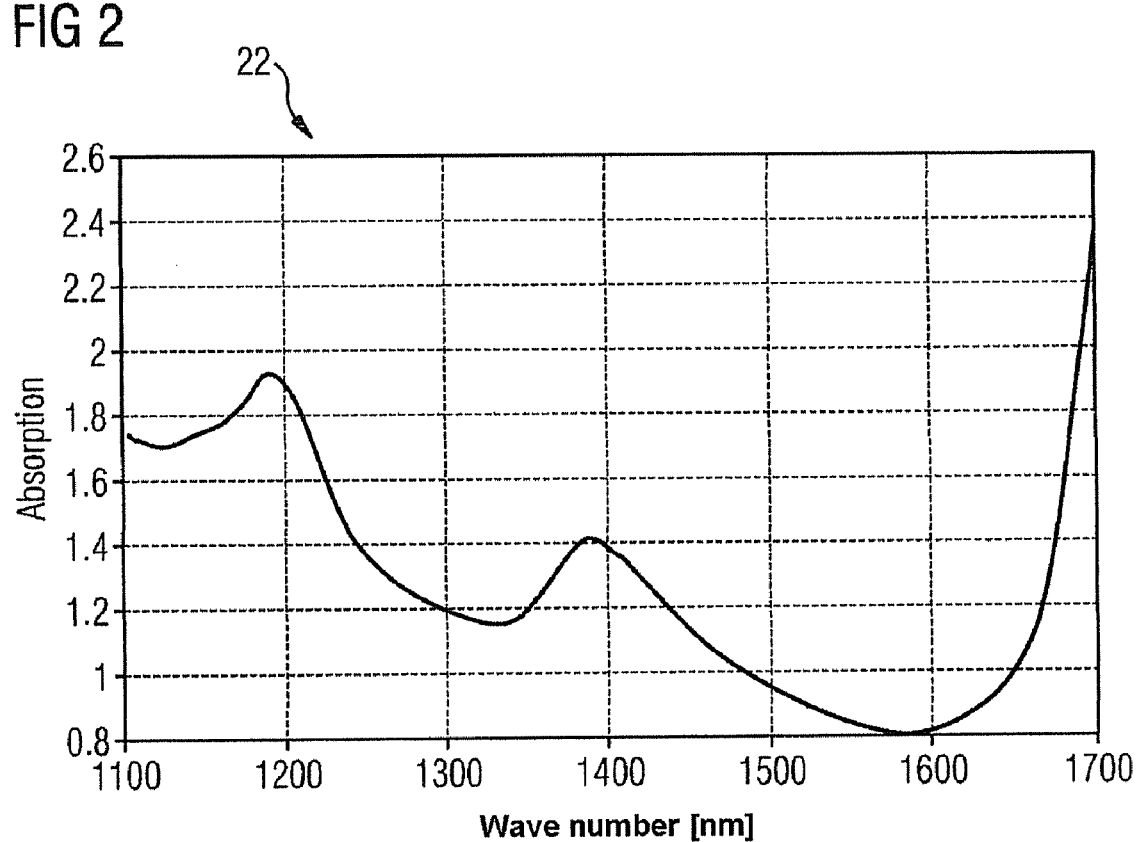
FIG. 2 shows the NIR spectrum of the ship's diesel from FIG. 1.

FIG. 2 shows in a graph 22 the NIR spectrum of the same sample as in FIG. 1. The spectrum was recorded by means of an NIR appliance of the company Boehringer Ingelheim MicroParts in the region of a wavelength (abscissa) of between 1100-1700 nm as transmission measurement. Here, too, the ordinate shows the absorption.

Figure 3:
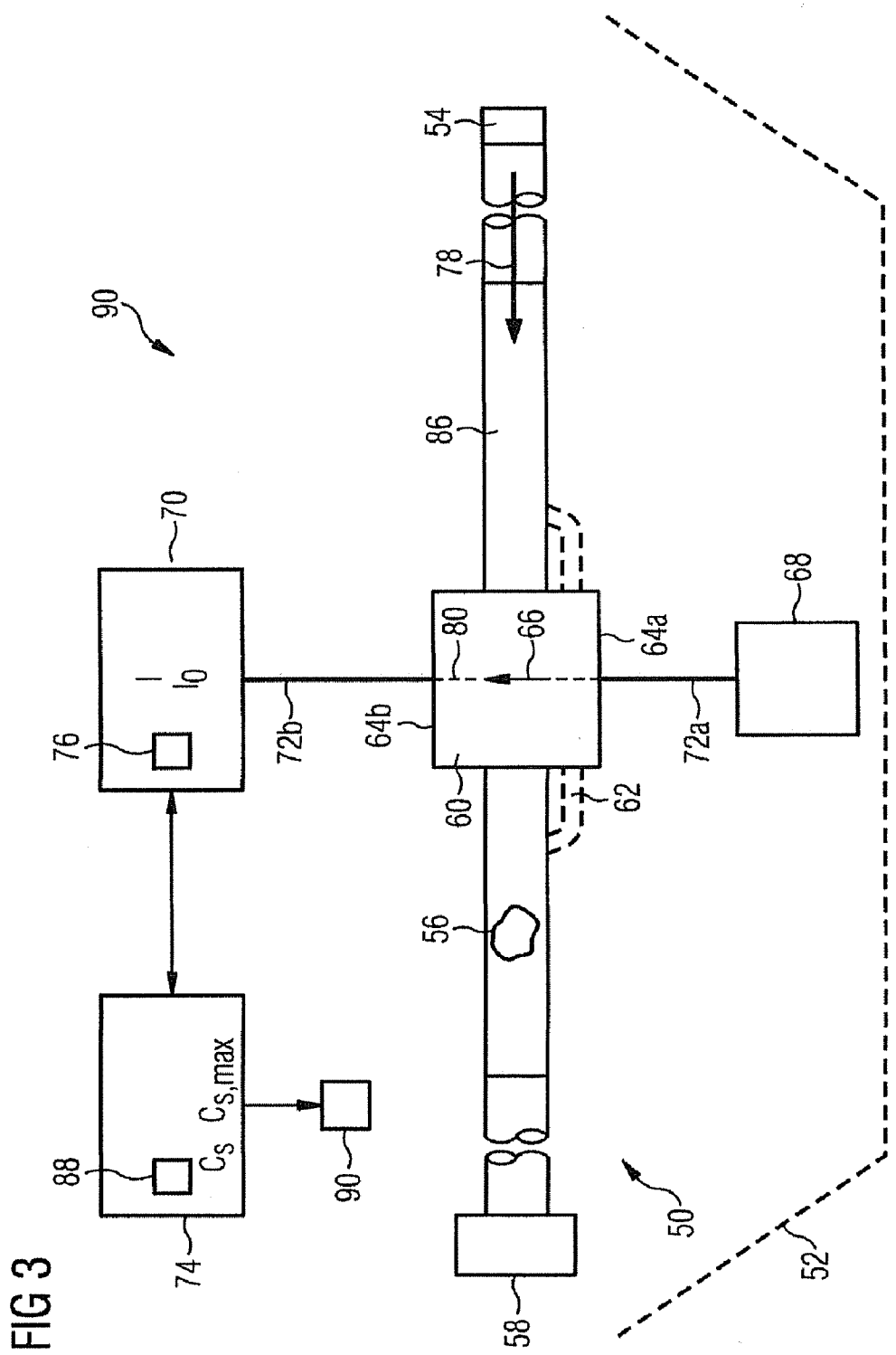
FIG. 3 shows a detail of the fuel path of a ship with a measuring device according to an embodiment of the invention having a transmission throughflow cell.

FIG. 3 shows, greatly simplified, a fuel path 50 in a ship 52, which fuel path continues from a filler neck 54 of the ship 52 as far as its engine 58 operated with diesel 56 which is representative of any fuels, such as diesel, heavy oil, gas oil, etc. In the ship 52, a measuring system 90 is installed. This is configured as follows: a measuring cell 60 designed as a transmission throughflow cell is arranged in the fuel path. In the example, the section of the inflow pipe 86 through which the fuel flows during the bunkering operation is shown. This is located in the main stream of the fuel 56 or alternatively, as illustrated by dashes, in a bypass line 62 and has the diesel (or, alternatively, part of this) flowing through it. The arrow 78 shows the direction of flow of the diesel 56.

The measuring cell 60 has two opposite windows 64a, b. These preferably consist of quartz glass or sapphire, and the optical path length is preferably set at between 0.1 and 10 mm, depending on the wavelength used for the light 66. The latter is generated by a light source 68 arranged on one side of the measuring cell 60. The light source 68 radiates in the NIR range. For this purpose, preferably, a tungsten halogen lamp is used, alternatively, for example, a globe for the MIR range. Opposite the light source 68 is arranged an IR spectrometer 70, preferably a microspectrometer for the NIR range or the MIR range.

The light is preferably conducted through optical fibers 72*a, b* from the light source 68 to the measuring cell 60 and from there to the spectrometer 70. Alternatively, the light source 68 and spectrometer 70 may also be flanged directly onto the measuring cell, so that the optical fibers 72*a, b* are dispensed with. A computer 74 serves for controlling the spectrometer 70 and for evaluating the spectra 76 measured by this.

Figure 4A:
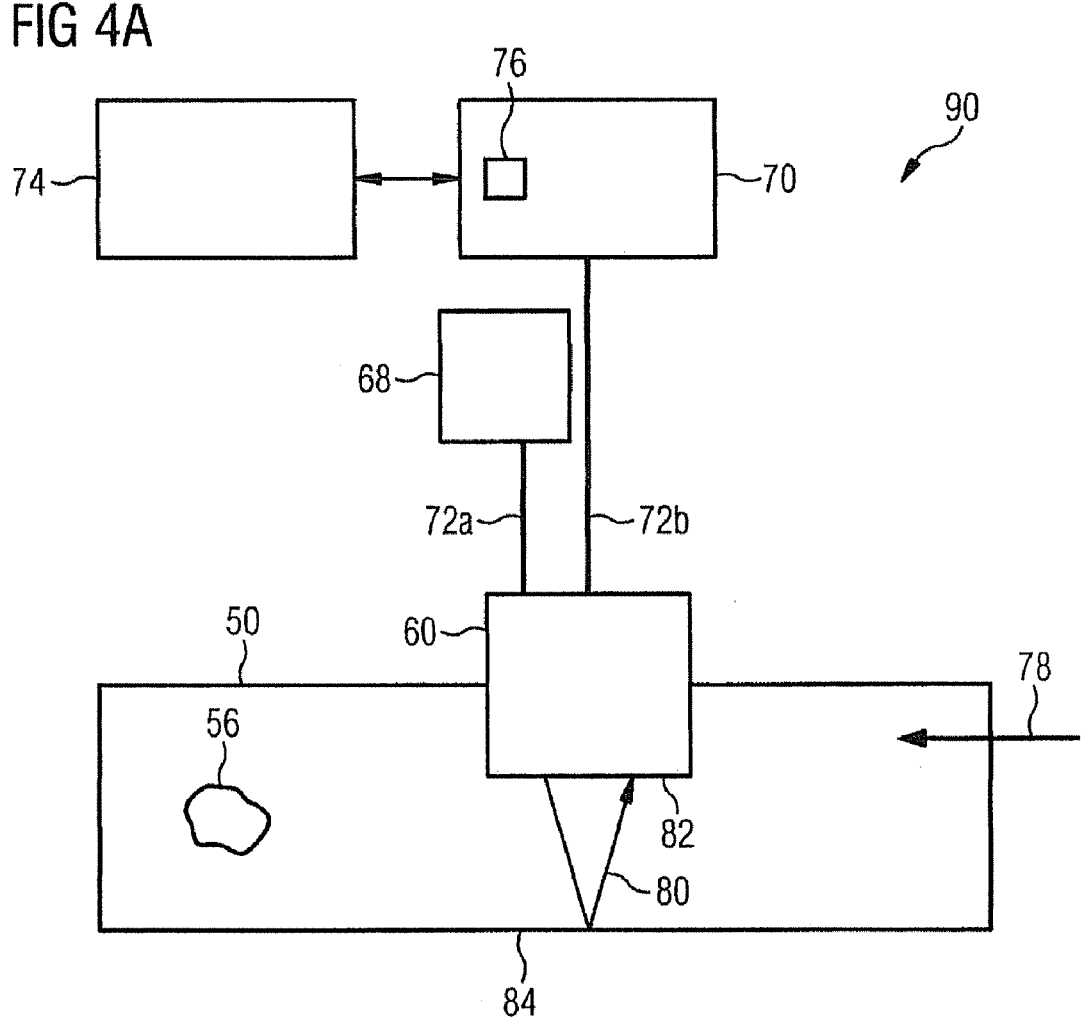
FIG. 4 shows an arrangement according to FIG. 3 with a reflection immersion cell (a) and with an ATR measuring cell (b)

FIG. 4*a* shows an alternative measuring system 90 to FIG. 3, in which the measuring cell 60 used is a reflection immersion cell. The optical path 80 through the diesel 56 is set here by means of the distance between the exit window 82 of the measuring cell 60 and the mirror 84.

FIG. 4*b* shows an alternative measuring system to FIGS. 3 and 4*a*, in which an ATR cell is used as the measuring cell 60. In this case, the ATR measuring cell is immersed in the fuel path 50 or the diesel 56. The optical path 80 is defined by the number of reflections, to be precise at least three.

Two different types of appliance are appropriate as a microspectrometer 70:
  line spectrometers, in which the spectral dispersion of the light is achieved by way of a fixed micromechanical reflection grating. One example is the NIR appliance of Böhringer Ingelheim MicroParts, in which the reflection grating is produced by means of the LIGA technique (light-induced galvanic forming).
  microspectrometers with moved micromirrors (MOEMS: micro-optical-electrical system), in which the dispersion of the light is generated by means of a reflection grating consisting of vaporized silicon. One example is the MOEMS—IR appliance of the company Colour-Control.

In FIG. 3 or 4*a, b*, a measurement takes place as follows:
1. Before the start of the bunkering operation, say the reception of diesel 56 through the filler neck 54 into the ship 52, the intensity $I_0$ (lamp spectrum) is determined when the inflow pipe 86 is empty. A check is made as to whether a required minimum light intensity $I_0 > I_{0,min}$ is achieved. If this is undershot, the control computer 74 outputs a fault message and demands the change of the light source 68 or the cleaning of the optical path 80.
2. After the start of the throughflow of the diesel 56, the measurement of the intensity I commences, this being converted into the absorption with the aid of the variable $I_0$.
3. The sulfur content $C_S$ of the diesel 56 is calculated from the measured absorption and from the calibration model 88 stored in the computer 74. This value may be indicated directly and/or stored in a bunker log 90. There may alternatively be provision for interrupting the bunkering operation automatically if a fixed limit value $C_S > C_{S,max}$ is overshot.

Figure 5:
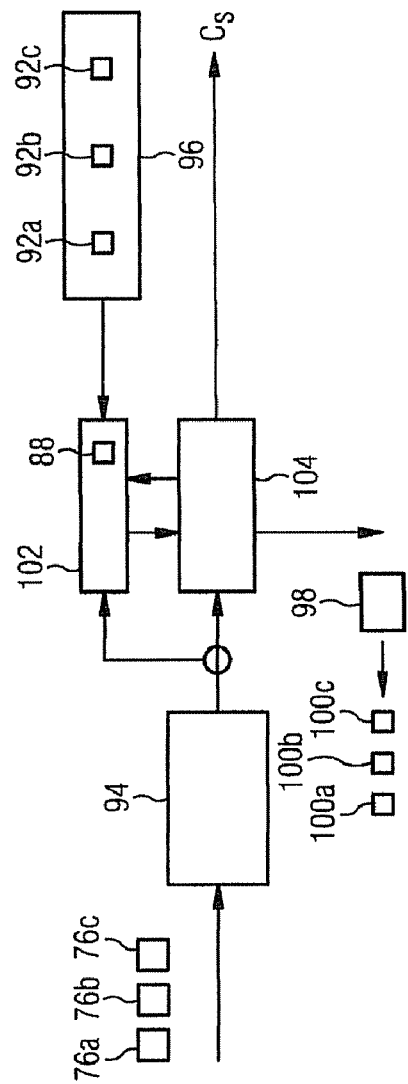
FIG. 5 shows a flowchart for a calibration model required for calculating the sulfur content in the ship's fuel.

The calibration model 88 required for calculating the sulfur content $C_S$ in the diesel 56 may be set up in the following way shown in FIG. 5:
1. The absorption spectra 76*a-c* of various ship's fuels, that is to say diesel 56, are determined. The sulfur content $C_S$ of these fuels has already previously been determined by means of known laboratory methods, that is to say is previously known and is stored in laboratory values 92*a-c*.

The optical set-up (type of measuring probe, optical path length, type of spectrometer and type of light source) and the ambient conditions (temperature, pressure) must be comparable to those under which the measuring system 90 is to be used later on ships 52. The laboratory analysis used as a reference, that is to say the laboratory values 92*a-c*, must have as low a measuring error as possible, since this measuring error is included as an error in the calibration model 88 and cannot be undershot.

2. A preprocessing 94 then commences. Incorrect measurements are removed there.
3. The spectra 76*a-c* are in this case smoothed or derivatives are formed.
4. The spectra 76*a-c* are also divided into a plurality of spectral regions.
5. The spectra 76*a-c* are divided into training and validation sets according to the customary methods (for example, venetian blind, leave-one-out).
6. The spectra 76*a-c* are standardized. For example, the following methods are appropriate: scaling, centering, minimum/maximum, vector standardization, orthogonal signal correction. The standardization factors of the training set are used to convert the spectra of the validation set.
7. In an evaluation 104, the spectra 76*a-c* are evaluated. Between the standardized absorption spectra 76*a-c* and the sulfur concentrations of the laboratory values 92*a-c* from the reference analysis, correlation models are calculated in a correlation step 96. For this purpose, the methods of main component regression (PCR) or of linear or nonlinear PLS (Partial Least Square) may be adopted.
8. The main components calculated by means of the PCR or PLS method may be used as input variables for a neural network 98.
9. The statistical parameters for describing the prediction error (RMSEP, RMSECV, BIAS) are calculated from calculated concentrations 100*a-c* of the validation set and from the laboratory values 92*a-c*. These statistical parameters form the bases of the optimal calibration model 88 which is used for application in the measuring system 90.
10. All the combinations (preprocessing, standardization, spectral regions, correlation methods) are tried out, and from these the optimal calibration model 88 is selected in the determination step 102.

The calibration model 88 may then consist of the following calculation instructions:
  type of preprocessing
  indication of the spectral regions
  standardization methods and standardization coefficients
  type of correlation method and main components from the PCR or PLS method
  if ANN methods are used, the data of the neural network
  the result of the calculations is the sulfur content $C_S$ of the ship's fuel, for example of the diesel 56.

Figure 6:
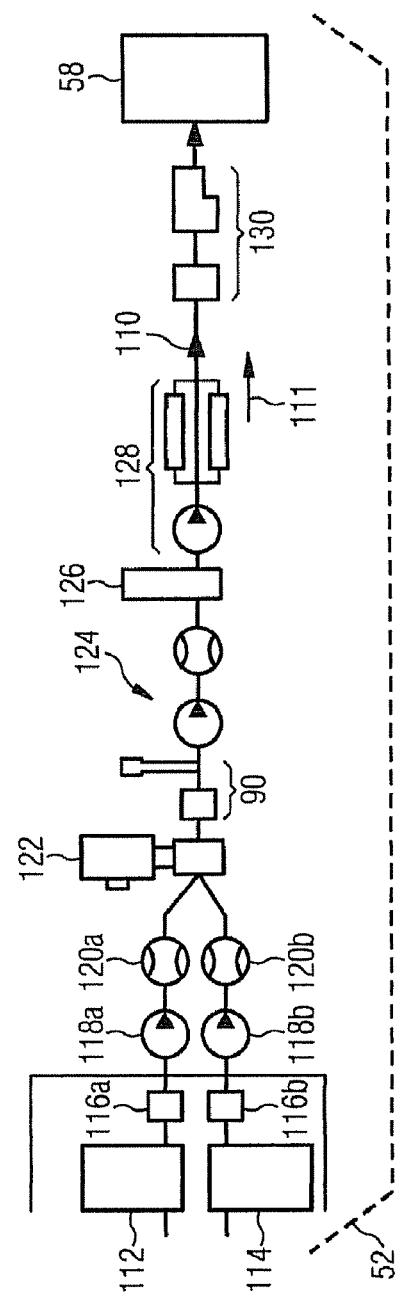
FIG. 6 shows a blending system for heavy oil with gas oil.

FIG. 6 shows the use of a measuring system 90 on board a ship 52 for the on-board blending of heavy oil (HFO) with gas oil. The aim is to produce a fuel 110 with a sulfur content $C_S$ of 1.49% for use in a sea area having a permitted 1.5% sulfur content, that is to say, for example, for traveling through SECA areas (North Sea and Baltic Sea, West coast of the USA).

A heavy oil service tank 112, which contains fuel of the sulfur content $C_S \gg 1.5\%$, and a gas oil service tank 114 for fuel with a sulfur content $C_S$ in the range of 0.2-0.3%, with a respective filter 116*a, b*, are shown.

The two tanks are equipped with pumps 118*a, b* frequency-controlled by microprocessors, in each case with following flowmeters 120*a, b* for heavy oil and gas oil.

The two tank lines then issue into a homogenizer 122 for mixing the two types of fuel into the fuel 110. The homogenizer 122 is then followed by the measuring system 90 for determining the current sulfur content $C_S$. The measuring system 90 comprises, not illustrated, likewise a following flowmeter and a writing indicator or logger approved by authorities.

For measuring the overall volume flow of the fuel 110 along the arrow 111 with $C_S=1.49\%$, said measuring system is followed again by a pump 124 with flowmeter, a standpipe 126 as an equalizing tank, and a pump 128 with an end preheater and filter.

The fuel line finally issues in a viscosimat 130 which regulates the preheating capacity of the end preheater 128 for the purpose of achieving the required injection viscosity or final fuel temperature upstream of the engine injection pumps. The fuel then passes into the engine 58.

A combination of pumps 118a, b with flowmeters 120a, b and a homogenizer 122 has already been implemented, with a viscosity probe, as an assembly combination by the company SIT.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

The invention claimed is:

1. A fuel system for a floating unit, including a fuel path which extends from a filler neck as far as an engine, with the fuel system comprising:
   a measuring device, arranged in the fuel path such that at least part of fuel, when flowing along the fuel path, flows through the measuring device, to measure a sulfur content of the fuel flowing through the measuring device;
   at least two fuel tanks for holding fuels of different sulfur content;
   a mixing device to mix fuels of the at least two fuel tanks, and
   a regulating device, cooperating with the measuring device, to regulate a mixture ratio of the fuels.

2. The fuel system as claimed in claim 1, wherein the measuring device comprises
   a light source to irradiate the fuel with light, and
   a detector to detect at least one of the light irradiating the fuel and light reflected by the fuel.

3. The fuel system as claimed in claim 2, wherein the light source is an IR light source.

4. The fuel system as claimed in claim 3, wherein the detector is an IR spectrometer.

5. The fuel system as claimed in claim 2, wherein the detector is an IR spectrometer.

6. The fuel system as claimed in claim 2, wherein the measuring device comprises an evaluation unit for multivariate evaluation of at least one of the light irradiating the fuel and the light reflected by the fuel.

7. The fuel system as claimed in claim 1, wherein the measuring device is arranged in an inlet portion of the fuel path, through which inlet portion fuel flows at least during a bunkering operation.

8. The fuel system as claimed in claim 1, wherein the measuring device is arranged in a section of the fuel path through which fuel flows at least during the operation of an engine of the floating unit.

9. The fuel system as claimed in claim 1, further comprising:
   a logging device to log the sulfur content determined by the measuring device.

10. The fuel system as claimed in claim 1, wherein the floating unit is a ship.

11. A method for operating a floating unit including a fuel system with a fuel path extending from a filler neck as far as an engine, of the method comprising:
    arranging a measuring device in the fuel path such that at least part of fuel, when flowing along the fuel path, flows through the measuring device; and
    determining a sulfur content in the fuel flowing through the measuring device,
    wherein at least two fuels of different sulfur content are mixed during operation of the floating unit, and wherein a sulfur content of the mixed fuel is held at a value on the basis of the measured sulfur content.

12. The method as claimed in claim 11, wherein the sulfur content is determined in the measuring device with the aid of IR spectroscopy.

13. The method as claimed in claim 12, wherein the sulfur content is determined by a multivariate evaluation from spectra determined by way of the IR spectroscopy.

14. The method as claimed in claim 11, wherein the sulfur content in fuel supplied to a tank of the floating unit during a bunkering operation is determined.

15. The method as claimed in claim 11, wherein the sulfur content in fuel supplied during the operation to an engine of the floating unit is determined.

16. The method as claimed in claim 11, wherein the measured sulfur content is logged.

* * * * *